US008697141B2

(12) United States Patent
Ratcliff et al.

(10) Patent No.: US 8,697,141 B2
(45) Date of Patent: Apr. 15, 2014

(54) METHOD AND COMPOSITION FOR PREVENTING AND HEALING OSTEONECROSIS OF THE JAW

(75) Inventors: James L. Ratcliff, Pueblo West, CO (US); Michael Z. Marder, Suffern, NY (US); Robert W. Marder, Suffern, NY (US); Jessica Ward Dykstra, Tempe, AZ (US); Elena J. Young, Scottsdale, AZ (US); Esmeralda Ann Garcia, Scottsdale, AZ (US)

(73) Assignee: Micropure, Inc., Scottsdale, AZ (US)

( * ) Notice: Subject to any disclaimer, the term of this patent is extended or adjusted under 35 U.S.C. 154(b) by 161 days.

(21) Appl. No.: 12/547,420

(22) Filed: Aug. 25, 2009

(65) Prior Publication Data

US 2010/0074970 A1 Mar. 25, 2010

Related U.S. Application Data

(60) Provisional application No. 61/092,034, filed on Aug. 26, 2008.

(51) Int. Cl.
*A61K 33/00* (2006.01)
*A61P 19/00* (2006.01)

(52) U.S. Cl.
USPC .......................................... 424/661; 424/600

(58) Field of Classification Search
USPC .......................................................... 424/53
See application file for complete search history.

(56) References Cited

U.S. PATENT DOCUMENTS

| | | |
|---|---|---|
| 4,689,215 A | 8/1987 | Ratcliff |
| 4,696,811 A | 9/1987 | Ratcliff |
| 4,786,492 A | 11/1988 | Ratcliff |
| 4,788,053 A | 11/1988 | Ratcliff |
| 4,792,442 A | 12/1988 | Ratcliff |
| 4,793,989 A | 12/1988 | Ratcliff |
| 4,808,389 A | 2/1989 | Ratcliff |
| 4,818,519 A | 4/1989 | Ratcliff |
| 4,837,009 A | 6/1989 | Ractliff |
| 4,851,213 A | 7/1989 | Ratcliff |
| 4,855,135 A | 8/1989 | Ratcliff |
| 4,886,657 A | 12/1989 | Ratcliff |
| 4,889,714 A | 12/1989 | Ratcliff |
| 4,925,656 A | 5/1990 | Ratcliff |
| 4,975,285 A | 12/1990 | Ratcliff |
| 5,200,171 A | 4/1993 | Ratcliff |
| 5,348,734 A | 9/1994 | Ratcliff |
| 5,489,435 A | 2/1996 | Ratcliff |
| 5,618,550 A | 4/1997 | Ratcliff |
| 5,738,840 A | 4/1998 | Richter |
| 6,077,502 A | 6/2000 | Witt et al. |
| 6,132,702 A | 10/2000 | Witt et al. |
| 6,136,348 A | 10/2000 | Ratcliff |
| 6,231,830 B1 | 5/2001 | Madray |
| 6,235,269 B1 | 5/2001 | Witt et al. |
| 6,251,372 B1 | 6/2001 | Witt et al. |
| 6,264,924 B1 | 7/2001 | Witt et al. |
| 6,350,438 B1 | 2/2002 | Witt et al. |
| 6,846,478 B1 | 1/2005 | Doyle et al. |

OTHER PUBLICATIONS

Nase et al., "Osteonecrosis of the jaw and oral bisphosphonate treatment." JADA 2006:137;1115-1119.*
Rautemaa et al., "Oral infections and systemic disease—an emerging problem in medicine." Clin Microbiol Ifect 2007:13;1041-1047.*
Marder et al., "Bisphosphonate-associated osteonecrosis: experiences in a private practice". Dent Today Oct. 2008, 27 (10); pp. 1-8.*
3M Peridex CHG 0.12% Oral Rinse; MSDS No. 25-8627-9 [Online]; 3M: St Paul, MN, Jul. 14, 2011, http://library.queensu.ca/research/guide/how-cite-chemical-literature/material-safety-data-sheets (accessed Apr. 30, 2012), 7pgs.
Corbin AC, et al. Antimicrobial penetration and efficacy in an in Vitro oral biofilm model. Antimicrob Agents Chemother 2011;55(7):3338-3344.
Daily Med: Current Medication Information. Chlorhexidine Gluconate Rinse [Xttrium Laboratories, Inc.]. Revised Feb. 2010. Available at: http://dailymed.nlm.nih.gov/dailymed/lookup.cfm?setid=34d15e72-8770-49dc-a514-d44ae4468a1e, 4 pgs.
Daily Med: Current Medication Information. Periogard (chlorhexidine gluconate) liquid [Colgate-Palmolive Company]. Revised Mar. 2010. Available at: http://dailymed.nlm.nih.gov/dailymed/lookup.cfm?setid=6e537d5f-bce1-41ce-9984-9b3c2861b7c9, 5 pgs.
Grootveld M, et al. Evidence for the microbicidal activity of a chlorine dioxide-containing oral rinse formulation in vivo. J Clin Dent 2001;12(3):67-70.
McBain AJ, et al. Effects of a Chlorhexidine Gluconate-Containing mouthwash on the vitality and antimicrobial susceptibility of in vitro oral bacterial ecosystems. Appl Environ Microbiol 2003;69(8):4770-4776.
Aas, JA, et al. Defining the normal bacterial flora of the oral cavity. J Clin Microbiol 2005;43(11):5721-5732.
Nase JB, Suzuki JB. Osteonecrosis of the jaw and oral bisphosphonate treatment. J Am Dent Assoc 2006;137:1115-1119.
Marder MZ, Marder RW. Bisphosphonate-Associated Osteonecrosis: Experiences in a Private Practice. Dent Today 2008;27(10):99-103, (9 pgs).

(Continued)

*Primary Examiner* — Walter Webb
(74) *Attorney, Agent, or Firm* — The von Hellens Law Firm, Ltd.

(57) ABSTRACT

A method and composition for preventing and treating all forms of osteonecrosis of the jaw are disclosed. The composition is comprised of 0.005%-2.0% weight/volume (w/v) chlorine dioxide source, such as sodium chlorite, chlorite ion, stabilized chlorine dioxide or similar and may take the form of a paste, gel, rinse, spray, powder, varnish or similar. The method for treatment and prevention includes the application of the composition in the oral cavity and other body areas affected by osteonecrosis of the jaw.

18 Claims, No Drawings

(56) References Cited

OTHER PUBLICATIONS

Soolari E, Soolari AM, Soolari AH. Phosphate buffer-stabilized 0.1% chlorine dioxide containing mouth wash facilitated sequestration of Bisphosphonate Related Osteonecrosis of the jaw (BRONJ) lesion from a patient who presented with Osteonecrosis of the jaw and a history of intravenous bisphosphonate use: a case report. Translational Biomedicine. 2010;1(7).

Soolari N, Soolari A. Closure of an open wound associated with bisphosphonate-related osteonecrosis of the jaw in a breast cancer patient. Open Dentistry Journal, 2011;5:1-5.

Ruggiero SL, Drew SJ. Osteonecrosis of the jaws and bisphosphonate therapy. J Dent Res. 2007;86 (11):1013-21.

Sedghizadeh PP, Kumar SK, Gorur A, et al. Identification of microbial biofilms in osteonecrosis of the jaws secondary to bisphosphonate therapy. J Oral Maxillofac Surg. Apr. 2008;66(4):767-775.

Mohammad AR, Giannini PJ, Preshaw PM, et al. Clinical and microbiological efficacy of chlorine dioxide in the management of chronic atrophic candidiasis: an open study. Int Dent J. Jun. 2004;54(3):154-158.

Wei MK, Wu QP, Huang Q, et al. Plasma membrane damage to Candida albicans caused by chlorine dioxide (ClO2). Lett Appl Microbiol. Aug. 2008;47(2):67-73.

Sharon A, Berdicevsky I, Ben-Aryeh H, et al. The effect of chlorhexidine mouth rinses on oral Candida in a group of leukemic patients. Oral Surg Oral Med Oral Pathol. Aug. 1977;44(2):201-5.

Wirthlin MR, Ahn BJ, Enriquez B, et al. Effects of stabilized chlorine dioxide and chlorhexidine mouthrinses in vitro on cells involved in periodontal healing. J West Soc Periodontol Periodontel Abstr. 2006;54(3):67-71.

Lubbers JR, Chauhan S, Miller JK, et al. The effects of chronic administration of chlorine dioxide, chlorite and chlorate to normal healthy adult male volunteers. J Environ Pathol Toxicol Oncol. Jul. 1984;5(4-5):229-38.

Werner CW, Seymour RA. Are alcohol containing mouthwashes safe? Br Dent J. Nov. 28, 2009;207(10):E19; discussion 488-9.

Lessa FC, Aranha AM, Nogueira I, et al. Toxicity of chlorhexidine on odontoblast-like cells. J Appl Oral Sci. Jan.-Feb. 2010;18(1):50-58.

Lee TH, Lee SS, Chou MY, et al. Cytotoxicity of chlorhexidine on human osteoblastic cells is related to intracellular glutathione levels. Int Endod J. May 2010;43(5):430-5.

Penn-Barwell JG, Murray CK, Wenke JC. Comparison of the antimicrobial effect of chlorhexidine and saline for irrigating a contaminated open fracture model. J Orthop Trauma. Aug. 7, 2012. (Epub ahead of print).

* cited by examiner

METHOD AND COMPOSITION FOR PREVENTING AND HEALING OSTEONECROSIS OF THE JAW

CROSS REFERENCE TO RELATED APPLICATIONS

The present application is related to and claims priority to a provisional application entitled "METHOD AND COMPOSITION FOR OSTEONECROSIS OF THE JAW" filed Aug. 26, 2008, and assigned Ser. No. 61/092,034.

BACKGROUND OF THE INVENTION

1. Field of the Invention

The composition is comprised of a 0.005%-2.0% weight/volume (w/v) chlorine dioxide source (sodium chlorite, chlorite ion, stabilized chlorine dioxide or similar) and may take the form of an oral paste, gel, rinse, spray, powder, tray, varnish or similar, to facilitate the healing of osteonecrosis of the jaw symptoms (including but not limited to necrotic bone lesions, inflammation and infection) and to prevent the development of osteonecrosis of the jaw. The method is the application of the composition in the oral cavity and all other areas of the body affected by osteonecrosis of the jaw to produce an antimicrobial effect, sanitize, debride, and penetrate, eliminate and control biofilms associated with osteonecrosis of the jaw, to facilitate the healing of osteonecrosis of the jaw symptoms and prevent the development of osteonecrosis of the jaw. The method may be applied daily or continuously as a treatment or prevention regimen for osteonecrosis of the jaw.

2. Description of Related Prior Art

Osteonecrosis is characterized by the formation of dead (necrotic) bone in various bones in the body, such as the femoral head or the jaw (mandible and/or maxilla). Pain and edema of surrounding tissue may accompany or precede this necrotic bone development.

Some forms of osteonecrosis are believed to develop due to either 1) decreased blood flow to bone which occurs as a result of a traumatic event or 2) non-traumatic factors. While the pathophysiology of all forms of osteonecrosis is currently unknown, some factors may potentially contribute to its development. These include bisphosphonate use, a compromised immune system, age, corticosteroid use, and tissue trauma. However, how these factors might contribute to the development of osteonecrosis is also unknown and still under investigation (AAMOS, 2007; Mariotti, 2008; Bejar et al., 2005).

Bisphosphonates are a class of drugs prescribed for diseases involving deleterious bone resorption, such as osteoporosis, bone cancer, or Paget's disease. In general, these drugs may be administered orally, intravenously, or parenterally and act by targeting osteoclasts in bone to inhibit and disrupt the bone resorption activity. The resulting function depends on the specific chemical structure of the bisphosphonate compound. Bisphosphonates are inorganic pyrophosphate analogues that contain two phosphonate groups along with $R^1$ and $R^2$ variable side chains all bound to a central carbon. Bisphosphonates localize to bone due to two phosphonate groups bonding to hydroxyapatite crystals and the variable group at the $R^1$ position (which may be a hydroxyl group that has a higher affinity for calcium than a halogen). After bone localization, the antiresorptive potency of the bisphosphonate is also dependent on the three-dimensional $R^2$ side chain conformation, the overall chemical structure, and both phosphonate groups (Russell, 2007).

Two subclasses of bisphosphonates with differing chemical structures and functions are: 1) nonaminobisphosphonates and 2) aminobisphosphonates, which contain an amino-nitrogen atom at the $R^2$ position. As these compounds lack an amino-nitrogen atom, nonaminobisphosphonates are more similar to inorganic pyrophosphate. Hence, osteoclasts "metabolically incorporate" nonaminobisphosphonates to form nonhydrolyzable adenosine triphosphate analogues, which in turn results in apoptosis of the osteoclast (Russell, 2007). Despite this occurrence, the presence of the amino-nitrogen atom at the $R^2$ position transforms aminobisphosphonates into more potent antiresorptive compounds than nonaminobisphosphonates (up to 10000-fold more potent). The main function of aminobisphosphonates involves inhibition of a key component of the mevalonate pathway (cholesterol synthesis), specifically the enzyme farnesyl diphosphonate synthase. Disruption of cholesterol synthesis is deleterious to various cellular activities in the osteoclast, which arrests osteoclast activity and ultimately bone resorption (Woo et al., 2006; Russell, 2007).

Since 2003, bisphosphonate-associated osteonecrosis of the jaw (ONJ) has been observed in patients receiving bisphosphonate therapy. ONJ is clinically diagnosed when an individual on a bisphosphonate drug regimen has necrotic bone lesion(s) on the jaw (mandible and/or maxilla) which persists for more than 8 weeks (without head or neck radiation being received by the patient simultaneously) (Estilo et. al., 2008; Woo et. al., 2006). There is no standard and reliable test to diagnose, anticipate or predict ONJ development. Therefore, ONJ is identified and diagnosed by the clinical definition after the onset and persistence of symptoms, through visual observation by the clinician and/or the use of medical imaging such as radiographs (Mariotti, 2008; Khosla et. al., 2007). Clinical staging of ONJ has been proposed to characterize the progression. At Risk stage comprises of individuals that exhibit no symptoms but are receiving either intravenous or oral bisphosphonates. Stage 1 involves the initial appearance of necrotic bone on the jaw but lacks the presence of infection. Stage 2 includes both the presence of necrotic bone on the jaw and infection, with associated pain. Stage 3 involves necrotic bone on the jaw, infection, pain "and one or more of the following: pathologic fracture, extraoral fistula, or osteolysis extending to the inferior border" (Ruggiero, 2008).

Patients receive bisphosphonates as primary and secondary therapies for diseases relating to abnormal bone resorption. Such patient populations include: 1) individuals at high risk for developing and diagnosed with osteoporosis, 2) bone cancer and multiple myeloma patients, 3) cancer patients at high risk for bone metastases, and 4) patients with Paget's disease (Ruggiero and Drew, 2007). Bisphosphonate therapies may be taken long-term (months to years), as is the case for the prevention and treatment of osteoporosis, where these drugs may be taken for up to a decade or more. Furthermore, bisphosphonates for cancer treatments may also be indicated over months as well. Since an individual may receive bisphosphonates over many months or years, a need exists for a long-term ONJ treatment and preventative that is safe and efficacious throughout the term of bisphosphonate therapy.

Since the pathophysiology of ONJ is unknown and there are no biomarkers to the development of the disease, the options for prevention are limited. One key prevention recommendation, however, is "to maintain good oral hygiene" and to receive a dental examination before beginning bisphosphonate therapy. Other recommended steps include having any needed invasive dental procedures prior to beginning a bisphosphonate regime and/or stopping bisphosphonate use prior to or during execution of the dental procedures (AAOMS, 2007; Khan, 2008). Refraining from smoking and minimizing alcohol consumption during bisphosphonate usage is also advised (Khan, 2008). ONJ preventative strategies vary according to the type of bisphosphonate being administered (intravenous versus oral) and the duration of use (Khosla, et al., 2007).

There is no standard treatment for ONJ. Currently, treatment is at the discretion of the clinician, dependent on a number of factors including the stage of the condition and duration of bisphosphonate use (Woo et al., 2006; Ruggiero 2008). One treatment involves the use of antibiotics with adjunct application of an anti-microbial oral rinse, such as the standard 0.12% chlorhexidine rinse (Ruggiero, 2008). Various studies examining the use of chlorhexidine with ONJ patients indicate that while it may help stop ONJ progression, it may not lead to assured ONJ resolution in all patients (Estilo et al., 2008). Other suggested treatments include, but are not limited to: hyperbaric oxygen therapy, surgical debridement/resection, halting bisphosphonate therapy, and use of other anti-bacterial oral rinses (AAOMS, 2007; Khosla et al., 2007; Ruggiero, 2008). Some treatments also include surgery, antibiotics, or debridement. The current goals for ONJ treatment are: 1) to preserve the patient's quality of life (through ONJ prevention, managing pain and secondary infection, and/or stopping progression of the condition) and 2) to enable oncology patients continued bisphosphonate use (AAOMS, 2007).

The specific association between bisphosphonates and ONJ development is not known nor has a direct causal link between bisphosphonate usage and the onset of ONJ disease been definitively established (ADA Council on Scientific Affairs Expert Panel ONJ, 2008; Mariotti, 2008). Certain factors however are believed to potentially increase an individual's risk for developing ONJ, such as: "1) history of dento-alveolar trauma, 2) duration of bisphosphonate exposure," and 3) the type and route of bisphosphonate administration such as oral versus intravenous (Ruggiero and Drew, 2007). Thus, ONJ prevalence and incidence are currently being investigated taking these factors into account. For example, one inquiry evaluating ONJ prevalence among oral alendronate users reported an ONJ prevalence rate of 4% in 208 patients (Sedghizadeh, et al., 2009). Furthermore, ONJ incidence in intravenous users may be as high as 12% as opposed to a reported 0.01% in oral users (Marder and Marder, 2008). It is also noted that aminobisphosphonates, such as pamidronate and zoledronic acid, are the bisphosphonate subclass most often associated with ONJ occurrence. One study stated that 94% of the reported ONJ patients had received zoledronic acid, pamidronate or a combination of the two drugs (Woo et al., 2006).

The pathophysiology of ONJ is unknown and currently under investigation. Many journal articles and reviews have been published evaluating the possible pathophysiology of this condition. One hypothesis suggested by Woo et al. (2006) is:

"... that bisphosphonate-associated osteonecrosis of the jaws results from marked suppression of bone metabolism that results in accumulation of physiologic microdamage in the jawbones, compromising biomechanical properties. Trauma and infection increase demand for osseous repair that exceeds the capacity of the hypodynamic bone, resulting in localized bone necrosis. The antiangiogenic property of bisphosphonates and other medications and the presence of other comorbid factors may promote the risk for or persistence and progression of this condition."

Along with the suppression of bone metabolism due to bisphosphonates, microbial biofilms are also hypothesized to be involved in ONJ. Biofilms are believed to be a source of microbial infection that can lead to development or increase progression of ONJ. According to Donlan and Costerton, "a biofilm is a microbially derived sessile community characterized by cells that are irreversibly attached to a substratum, interface or to each other, are embedded in a matrix of extracellular polymeric substances that they have produced, and exhibit an altered phenotype with respect to growth rate and gene transcription" (Donlan and Costerton, 2002). Multispecies microbial biofilms were recently identified in bone specimens from ONJ lesions of four ONJ patients (Sedghizadeh et al., 2008). Specific pathogens classified in these ONJ biofilms were from genera such as: *Fusobacterium, bacillus, actinomyces, staphylococcus, treponemes,* and *Candida,* among others. The bacteria ranged from gram-positive and gram-negative organisms and included aerobes, although anaerobes and facultative anaerobes dominated. Known morphotypes of the *Candida* species were also apparent in the ONJ biofilm of all four subjects and co-aggregation with bacteria also was observed. Sedghizadeh et al. further observed the absence of eukaryotic cells and the presence of microorganisms in the bone resorption pits of osteonecrotic bone specimens, indicating that microorganisms possibly directly contribute to bone resorption as well. Taken together, the presence of biofilms in ONJ may potentially contribute to development and progression (Sedghizadeh et al., 2008).

The ADA Council on Scientific Affairs Expert Panel on ONJ (2008) mentioned a second hypothesis that the bisphosphonate compounds themselves are toxic to the tissues vulnerable to ONJ development. Preliminary in vitro evidence on oral mucosal cells (human gingival fibroblasts and keratinocytes) indicates that direct application of zoledronic acid has a deleterious effect on the life of these cells (Scheper et al., 2008). Specifically, these cells experience gene-regulated induced apoptosis when zoledronic acid at low concentrations is applied. Apoptotic genes activated by zoledronic acid include TNF, BCL-2, Caspase, IAP, TRAF (Scheper et al., 2008). As a result, direct toxicity to oral mucosal cells by bisphosphonates may also be a factor in ONJ development.

The term chlorine dioxide ($ClO_2$) is widely used in the industry. Those skilled in the art will and do appreciate the various forms or variations thereof which are available to perform certain intended functions and purposes. U.S. Pat. No. 3,271,242 describes a form of stabilized chlorine dioxide and a method of making it which form is particularly useful in carrying out the present invention. The 1979 text Chlorine Dioxide, Chemistry and Environmental Impact of Oxychlorine Compounds, describes (aqueous) stabilized chlorine dioxide as follows:

"The stabilization of chlorine dioxide in aqueous solution was proposed by using perborates and percarbonates. Thus, a stabilized solution of $ClO_2$ would be obtained at pH 6 to 8 by passing gaseous $ClO_2$ into an aqueous solution containing 12% $Na_2CO_3.3H_2O_2$. Other variants are possible. In reality, it seems that in these methods, the chlorine dioxide is practically completely transformed to chlorite. Dioxide is released upon acidification..." [Masschelein, 1979]

The term 'peroxy compounds' may substitute for 'percarbonates and perborates', referring to any buffer suitable for maintaining the pH and hence, the stability of the $ClO_2$ in solution. The buffer is a necessary component, as the $ClO_2$ is unstable at low pH. Once the solution reaches low pH or encounters an area of low pH, the stabilized $ClO_2$ is released from solution and available for sanitation and oxidation.

Prior to its use in the 1950s, chlorine dioxide was a known to have bactericidal properties (Masschelein, 1979). In U.S. Pat. No. 2,451,897 Woodward first established use of chlorine dioxide to eliminate the unpalatable taste in shrimp; thereafter, chlorine dioxide began to be used for its oxidative properties in various industries for different applications. Chlorine dioxide has been applied to bleaching cellulose fibers to facilitate the manufacture of wood pulp. Furthermore, chlorine dioxide has been used to disinfect water for public consumption with minimal effect on taste. Chlorine dioxide provides a beneficial alternative over other processes involving the use of ozone and bleach, due to the fact that chlorine dioxide costs less to use, creates less toxicity, and creates fewer chlorinated by-products (Masschelein, 1979).

Biofilm growth is a problem which occurs in dental unit water lines (DUWL). Some of the microbe genera detected in DUWL biofilms are *Actinomyces, Bacillus, Mycobacteria, Pseudomonas, Sphingomonas, Staphylococcus*, and *Streptococcus*. Stabilized chlorine dioxide solutions have been previously shown to be an effective decontaminant on biofilms that form in DUWLs. A specific study yielded results that indicated that stabilized chlorine dioxide outperformed alkaline peroxide in managing biofilm growth, by retaining a hetertropic plate count (HPC) value of 0 after 5 days of treatment (Wirthlin et al., 2003).

In oral care products, the use of stabilized chlorine dioxide has been suggested as an active ingredient by a number of patents: U.S. Pat. Nos. 4,689,215; 4,696,811; 4,786,492; 4,788,053; 4,792,442; 4,793,989; 4,808,389; 4,818,519; 4,837,009; 4,851,213; 4,855,135; 4,886,657; 4,889,714; 4,925,656; 4,975,285; 5,200,171; 5,348,734; 5,489,435; 5,618,550. Additionally, the use of stabilized $ClO_2$ has been suggested for the degradation of amino acids in U.S. Pat. No. 6,136,348. The premise for these products is that the stabilized chlorine dioxide will remain as such until it encounters the localized reductions in pH. Reduced pH levels can be a result of low pH saliva or oral mucosa, the accumulation of oral disease-causing bacteria or the presence of plaque biofilms on teeth and epithelial cells. Once released, the now active chlorine dioxide is effective at killing bacteria and oxidizing volatile sulphur compounds (VSCs). VSCs have been shown to enable oral infections and inflammation as well as produce oral malodor. Data have shown dramatic reduction in bacteria after exposures as short as 10 seconds, as set forth in U.S. Pat. No. 4,689,215. Additional data show remarkable decrease in VSCs in expired mouth air; the mechanism is believed to be oxidation of VSCs through the cleavage of the sulfide bonds.

Richter (U.S. Pat. No. 5,738,840) teaches the use of a two part system to deliver molecular chlorine dioxide to the oral cavity. This method relies on the use of a metal chlorite salt mixed with a metal hypochlorite salt (such as sodium hypochlorite) to form molecular chlorine dioxide (between 3 and 200 parts per million (ppm)). The application of this method is to treat halitosis. Madray further instructs on a method to make molecular chlorine dioxide (U.S. Pat. No. 6,231,830). Madray indicates mixing an alkali metal chlorite with an alkali metal iodide to produce molecular chlorine dioxide, but also indicates that these two entities should not be mixed until the chlorine dioxide is necessary, in order to ensure long shelf-life. Madray describes the use of this invention to treat gum disease, acne, and dandruff, along with additional ailments and conditions.

The delivery of chlorine dioxide precursors, such as the chlorite ion, to the mouth is taught by Witt (U.S. Pat. Nos. 6,077,502; 6,132,702; 6,235,269; 6,251,372; 6,264,924; and 6,350,438). Witt teaches the delivery of the chlorite ion to the oral cavity, via various delivery systems including oral rinse, using formulations with minimal chlorine dioxide (50 ppm or less) and at a pH greater than 7. Witt's patents also teach the use of these formulations to treat malodor, gingivitis, periodontitis, osteomyelitis of the jaw, and infectious stomatitis, among other applications.

Doyle (U.S. Pat. No. 6,846,478) teaches that topical oral application of a "safe and effective" amount of the chlorite ion (pH greater than 7 and 0.02-6.0% (w/v)) can control bacteria-mediated diseases and promote whole body health. The inventors claim that periodontal disease may be related to increased risk of developing certain diseases and that the chlorite ion is an antimicrobial that is selective for gram negative anaerobes that cause periodontal diseases (*P. gingivalis, B. forsythus, A. actinomycetemcomitans, T. denticola, T. socranskii, F. nucleatum*, and *P. intermedia*). Therefore, Doyle claims that since the chlorite ion prevents "the spread of bacteria" via the oral cavity and thereby helps control systemic oral pathogenic infections that increases risk for these "bacteria-mediated" diseases, the chlorite ion promotes whole body health. Furthermore, Doyle claims the chlorite ion is able to reduce specific biomarkers of these diseases. Doyle cites the chlorite ion's ability to specifically reduce disease risk of atherosclerosis, diabetes, stroke, severe respiratory diseases, bacteremia, and those at risk for delivering pre-term low birth weight babies.

While the prior art teaches various compositions of chlorine dioxide and chlorine dioxide precursors relative to general oral health, gum disease and oral malodor, these sources do not teach the effectiveness of such compositions on biofilms found on the treatment of osteonecrosis of the jaw or preventing the onset of osteonecrosis of the jaw.

SUMMARY OF THE INVENTION

The composition is comprised of a 0.005%-2.0% (w/v) chlorine dioxide source (sodium chlorite, chlorite ion, stabilized chlorine dioxide or similar) and may take the form of an oral paste, gel, rinse, spray, powder, tray, varnish or similar, to facilitate the prevention and healing of osteonecrosis of the jaw including but not limited to necrotic bone lesions, inflammation and infection. The related methodology includes the application of the composition in the oral cavity and all other areas of the body affected by osteonecrosis of the jaw to produce an antimicrobial effect, sanitize, debride, and penetrate, eliminate and control osteonecrosis of the jaw biofilms associated with osteonecrosis of the jaw which facilitates the healing of osteonecrosis of the jaw symptoms and prevents the development of osteonecrosis of the jaw. The application may be daily or continuously as an osteonecrosis of the jaw treatment regimen or as an osteonecrosis of the jaw prevention regimen.

A primary object of the present invention is to provide a composition, in a concentration in the range of about 0.005% to about 2.0% (w/v), to facilitate the healing of osteonecrosis of the jaw including but not limited to necrotic bone lesions, inflammation and infection and to prevent the development of osteonecrosis of the jaw.

Another object of the present invention is to facilitate healing of osteonecrosis of the jaw symptoms by the application of the composition to the oral cavity and other osteonecrosis of the jaw affected tissues.

Yet another objective of the present invention is to prevent development of osteonecrosis of the jaw by the application of the composition to the oral cavity or other areas of the body susceptible to the development of osteonecrosis of the jaw.

Still another object of the present invention is for the composition to produce antimicrobial, sanitizing, and debriding effects on tissues affected by or susceptible to osteonecrosis of the jaw and facilitate healing of osteonecrosis of the jaw symptoms and prevent of osteonecrosis of the jaw.

A further object of the present invention is for the composition to penetrate, eliminate and control biofilms that form over tissues that are affected by or susceptible to osteonecrosis of the jaw.

Yet a further object of the present invention is to apply the composition on a daily or continuous basis to the oral cavity or all other areas of the body affected by osteonecrosis of the jaw.

A still further object of the present invention is to apply the composition upon the onset of osteonecrosis of the jaw symptoms (including but not limited to, necrotic bone lesions, inflammation, and infection) and/or prior to or throughout bisphosphonate use.

These and other objects and specific embodiments of the present invention will become apparent to those skilled in the art as the description thereof proceeds.

DESCRIPTION OF THE PREFERRED EMBODIMENT

Potential Mechanism of Action of the Invention

The pathophysiology of osteonecrosis of the jaw and bisphosphonate-associated osteonecrosis of the jaw (ONJ) are unknown. Therefore, any suggested mechanism of action for the chlorine dioxide source (sodium chlorite, chlorite ion, stabilized chlorine dioxide or similar) composition is hypothesized on the following: 1) published experimental evidence investigating ONJ, 2) previous work describing the treatment of malodor, gingivitis, and periodontitis, 3) previous work describing the properties of chlorine dioxide sources and 4) previous work investigating biofilms and describing the effect of chlorine dioxide sources on biofilm.

A possible means for prevention and treatment of ONJ is based on the hypothesis that bisphosphonates are anti-angiogenic, depriving tissues of nutrients, leading to the presence of microbes which in turn impedes the healing process of tissues existing in a depressed metabolic state (Adornato et al., 2007; Woo et al., 2006). Furthermore, the mode of action is also based on the hypothesis that biofilms involved with ONJ are associated with conditions that may lead to ONJ development and progression (Sedghizadeh et. al., 2008). It is hypothesized that the present invention produces an antimicrobial effect, sanitizes, and debrides ONJ based on previous work which investigated the microbicidal activity, sanitizing, and debriding properties of chlorine dioxide containing oral rinse (Grootveld, et. al., 2001; U.S. Pat. No. 4,855,135; 4,818,519; 4,886,657); Mohammad et. al., 2004; Wei et. al., 2008). It is believed that the present invention may penetrate, eliminate, and control biofilms (biofilms which may contain microorganism species such as *Candida* or *Streptococcus*) that form over ONJ lesions or tissues susceptible to ONJ formation. This assumption is based on work investigating the characteristics of biofilms on ONJ lesions, and the ability of a chlorine dioxide source to decontaminate biofilms as well as the microbicidal properties of chlorine dioxide (Wirthlin et. al., 2003; Sedghizadeh et. al., 2008; U.S. Pat. No. 4,818,519; 4,886,657; Mohammad et. al., 2004; Wei et. al., 2008). It is further thought that the present invention results in less extensive toxic effects on ONJ-associated cell types, associated with wound healing, compared with alternative oral rinses currently used to prevent and treat ONJ, thereby facilitating healing of ONJ or preventing ONJ development (Wirthlin et. al., 2006; Patel el. al., 2006; Gianelli et. al., 2008; Nishikori, et. al., 2008). Thus, by the presumed ability of a chlorine dioxide source (sodium chlorite, chlorite ion, stabilized chlorine dioxide or similar) to act as an antimicrobial, sanitize, debride, penetrate, eliminate and control ONJ biofilms, and reduce the toxicity to cells that are critical to wound healing, the present invention provides an antiseptic environment that facilitates healing of ONJ symptoms and results in the subsequent resolution of ONJ symptoms. Anecdotal observation of application of a chlorine dioxide source on ONJ provides preliminary evidence of treatment and possibly prevention (Marder and Marder, 2008).

Evidence for Mechanism of Action

EXAMPLE 1

Chlorine Dioxide Source Potential Efficacy as an ONJ Treatment (Marder and Marder, 2008)

Dr. Michael Z. Marder and Dr. Robert W. Marder observed that the use of CloSYS (a registered trademark) oral rinse (0.1% stabilized chlorine dioxide oral rinse, Rowpar Pharmaceuticals Inc. Scottsdale, Ariz.) resulted in the resolution of ONJ lesions. Four subjects were observed to have ONJ lesions and associated symptoms on the jaws. One ONJ patient was treated with mechanical intervention and antibiotic therapy. The remaining three ONJ patients were treated with the application of CloSYS oral rinse onto the ONJ lesions.

The patient treated by antibiotic therapy had been receiving intravenous zoledronate (Zometa, Novartis; East Hanover, N.J.), as well as carboplatin (Paraplatin, Bristol Laboratories Oncology Products, Bristol-Meyers Squibb Co.; Princeton, N.J.), etoposide (VePesid, Bristol Laboratories Oncology Products, Bristol-Meyers Squibb Co.; Princeton, N.J.), and docetaxel (Taxotere, Aventis Pharmaceutical Products Inc.; Parsippany, N.J.). The patient presented a bone lesion that was smoothed and then treated with an antibiotic (Augmentin, SmithKline Beecham Pharmaceuticals: Philadelphia, Pa.). Observations continued for a little over a year, and the lesion continued to increase in size and did not heal with this antibiotic regimen.

Three patients presenting ONJ lesions had received or were currently receiving long-term alendronate therapy (Fosamax, Merck & Co Inc.; Whitehouse Station, N.J.). Two of these patients underwent tooth extractions either prior to or while on the alendronate therapy. All three patients were instructed to rinse with CloSYS oral rinse for thirty seconds, three to four times a day. The patients experienced complete healing of the ONJ lesions and affected tissue within a year of initial use of CloSYS oral rinse. An example of healing was shown by gingival healing and closure of the diseased area with no bone exposure.

EXAMPLE 2

Antimicrobial, Sanitizing, and Debriding Properties of a Chlorine Dioxide Source In 2001, Grootveld et. al. published a study that reported the effect of a chlorite ion/chlorine dioxide mixture (RetarDEX (a registered trademark) oral rinse, Rowpar Pharmaceuticals, Inc.) to reduce levels of *Streptococcus mutans, lactobacilli,* and *Candida albicans* in human saliva. The experimental group of 33 subjects rinsed with 20 ml of RetarDex oral rinse three times daily for 60 seconds, and continued this regimen for 14 days. An independent negative control group of 10 subjects rinsed with 20 ml of mineral water for 60 seconds, and continued this regimen for 14 days. Saliva was collected from both groups at baseline and 14 day follow-up. RetarDEX oral rinse was shown to significantly reduce bacterial counts of *S. mutans* and *lactobacilli* in saliva, however the reduction of *C. albicans* was not found to be significant. (Grootveld et. al., 2001)

U.S. Pat. No. 4,818,519 describes a method for stabilized chlorine dioxide to prevent and reduce plaque formation. U.S. Pat. No. 4,886,657 describes a method for stabilized chlorine dioxide to prevent periodontitis by reducing and preventing plaque formation. U.S. Pat. No. 4,855,135 describes a method for stabilized chlorine dioxide to debride oral wounds by reducing and preventing plaque formation. All of these patents cite evidence of the in vitro activity of 200 ppm of a stabilized chlorine dioxide solution to kill *S. mutans* and *Bacteroides gingivalis*. In the case of *S. mutans,* 200 ppm of stabilized chlorine dioxide had a 99% in vitro kill rate within 10 seconds of application. In the case of *B. gingivalis,* 200 ppm of stabilized chlorine dioxide had various in vitro kill rates dependent on the treatment time, and at several time points and different pH, 100% kill was observed.

In previous studies, a chlorine dioxide source has also been shown to be effective against *Candida albicans*. One such study conducted by Mohammed et. al. (2004) examined the efficacy of a chlorine dioxide oral rinse to treat chronic atrophic candidiasis in thirty elderly subjects. These subjects rinsed for one minute with a 0.8% chlorine dioxide oral rinse, two times a day, for 10 days (the subjects also soaked their dentures in the oral rinse overnight for 10 days). Clinical and microbiological evaluations were performed after completion of the protocol (post day 10) and the results were compared with baseline measurements. The results of the clinical and microbiological data were statistically significant. In the case of the clinical results, most patients experienced "complete resolution" of the condition. With reference to the microbiological data, the total CFU/ml of *C. albicans* was between 15000-53000 at time zero, and after ClO2 exposure (post day 10), the total CFU/ml was less than 500.

Wei et. al. (2008) performed an experiment to investigate a potential mechanism of action of chlorine dioxide against *C. albicans*. This study examined the ability of chlorine dioxide to damage the plasma membrane of *C. albicans*. *C. albicans* was exposed to varying concentrations of stabilized chlorine dioxide, and plasma membrane damage was assessed over a time or dose dependent evaluation. Plasma membrane damage was evaluated by measuring the leakage of potassium and adenosine triphosphate (ATP), as well as by determining the "alteration of ultrastructures, membrane potential, and membrane integrity." A marked increase in potassium leakage was observed in a time and dose dependent manner, indicating that chlorine dioxide potentially causes permeation of the plasma membrane of *C. albicans*.

EXAMPLE 3

Chlorhexidine Inability to Resolve ONJ and Treat ONJ

A retrospective study was conducted of 4,835 intravenous bisphosphonate users treated at Memorial Sloan-Kettering Cancer Center (MSKCC). Memorial Sloan-Kettering Cancer Center Dental Service received 310 of these patients referred between Jan. 1, 1996 and Jan. 31, 2006. Thirty-five of these individuals were diagnosed with ONJ either at the initial dental evaluation or a subsequent dental visit and all were treated with 0.12% chlorhexidine as part of the ONJ treatment regimen. Eleven patients did not reach the end point of the study. Out of the remaining 24 patients treated with chlorhexidine, only 3 patients experienced ONJ resolution, while the other 21 patients either experienced ONJ progression (13 patients) or experienced no change in ONJ status (8 patients) (Estilo et. al., 2008).

EXAMPLE 4

Evidence of Chlorhexidine versus Chlorine Dioxide Toxicity to Cells

Cells potentially involved in ONJ development and progression are fibroblasts, osteoblasts, and endothelial cells. Several studies have been published that investigate the effects of chlorhexidine exposure (and chlorine dioxide exposure) on each of these cell types.

A study examined the toxicity of stabilized chlorine dioxide versus chlorhexidine on human gingival fibroblasts, periodontal ligament cells, and osteoblasts. One of the measures of cell toxicity was an assay for levels of lactate dehydrogenase (LDH) when these cell types were exposed to respective oral rinses. LDH is released by cells when the plasma membrane is damaged. The results show that exposure of the fibroblasts, periodontal ligament cells, and osteoblasts to stabilized chlorine dioxide did not increase the release of LDH when compared with controls. In all three cell types, however, exposure of cells to 0.12% chlorhexidine did show elevated and significant LDH release compared with controls. (Wirthlin et al., 2006)

Patel et al. conducted a study on the cytotoxicity of chlorhexidine on human osteoblast-like cells using a cell culture model. Cell survival increased as the concentration of chlorhexidine decreased, and subsequently, a decrease in exposure to chlorhexidine over time also increased cell life. The work indicates that there is an adverse effect on the survival of osteoblast-like cells exposed to high concentrations of chlorhexidine over a prolonged time interval (Patel et al., 2006).

Gianelli et al. further studied in vitro toxicity of chlorhexidine digluconate on various cell types including osteoblasts, fibroblasts, and endothelial cells. Cell viability and cell death of these cell types were measured upon exposure to chlorhexidine. This study found that chlorhexidine induced apoptosis and led to necrosis of these cell types, in a dose and time dependent manner. Thus, this work helps further substantiate the Patel's work. (Gianelli et al., 2008)

Nishikori et al. conducted a study investigating the effects of chlorine dioxide versus hydrogen peroxide on cell survival of human gingival fibroblasts. Chlorine dioxide was shown not to induce apoptosis significantly at the tested concentrations (0.05 mM $ClO_2$, 0.1 mM $ClO_2$, and 0.5 mM $ClO_2$), whereas hydrogen peroxide induced apoptosis at all concentrations tested (0.05 mM, 1.0 mM). (Nishikori et al., 2008)

EXAMPLE 5

Evidence of Anti-Angiogenic Effects of Bisphosphonate

Research evidence cited by Adornato et al indicates certain bisphosphonates negatively affect vascularity due to anti-angiogenic effects on bone. Specifically, pamidronate was shown to reduce bone vascularity in rats. Both zoledronic acid and pamidronate displayed the ability to inhibit the new formation of capillaries from blood vessels (capillary neoangiogenesis). (Adornato et al., 2007) The possible effects these drugs have on angiogenesis and bone vascularity indicate a potential explanation of ONJ pathophysiology, as both drugs are known to be associated with ONJ (Woo et. al., 2006).

EXAMPLE 6

Evidence of Biofilm and Microbes in ONJ and the Ability of Chlorine Dioxide to Penetrate and Decontaminate Biofilms Microbial biofilms have been detected in osteonecrotic regions of the jaw and some microbial genera that comprise these biofilms have been identified by Sedghizadeh et al. (2008). Of the microbial genera identified in ONJ biofilms, similar genera have also been detected in biofilms that occur in dental unit waterlines (DUWL)—genera such as *Actinomyces* spp, *Bacillus* spp, *Staphylococcus*, and *Streptococcus*. (Wirthlin et al., 2003; Sedghizadeh et al., 2008)

Wirthlin et. al.'s (2003) study measured the heterotrophic plate count (HPC) of samples taken from DUWL biofilms that were treated with different DUWL cleaners. The study provided evidence that a highly concentrated stabilized chlorine dioxide solution (MicroClear Dental Unit Waterline Cleaner, Rowpar Pharmaceuticals, Inc.) was able to penetrate and decontaminate DUWL biofilms. It is noted that HPC measures a wide variety of microorganisms and the specific microbal species found in the DUWL biofilms were not individually identified. Also, DUWLs are surfaces that provide an environment which differ in composition and physical conditions from the oral cavity, therefore these differences should be taken into consideration as variables that make ONJ biofilms differ from DUWL biofilms. (Wirthlin et. al., 2003)

Villhauer et. al. presented evidence of bactericidal activity of stabilized chlorine dioxide against polymicrobial biofilms (2009). The bacteria included in the experiment were specific to periodontal pathogens such as *Actinomyces viscosus, Streptococcus sanguinis, Fusobacterium nucleatum, Peptostreptococcus micros*, and *Porphyromonas gingivalis*. Cultured biofilms were exposed to one minute regimens of a 0.5% (w/v) stabilized chlorine dioxide oral rinse. The results of this study showed that multiple exposures to the oral rinse: 1) reduced bacterial counts of *S. sanguis* by 2-3 logs, 2) eliminated almost all counts of *P. gingivalis, P. micros* and *F. nucleatum*, and 3) had little to no effect on counts of *A. viscosus*. Single exposure to the oral rinse yielded no significant bacterial counts. While this evidence may be encouraging, periodontal pathogens inhabit a different anatomical and cellular environment than ONJ biofilms. Periodontitis refers to a group of infections in which the supporting tissues of the teeth such the as gingiva, periodontal ligament and alveolar bone are destroyed by plaque-induced inflammation, whereas, ONJ is known to involve jaw-bone necrosis of the maxilla and/or mandible due to unknown factors. Furthermore, the specific microbial species found in ONJ biofilms have not been completely identified and whether biofilms play a role in ONJ has not been established. Therefore, Villhauer et al.'s research should be considered evidence that stabilized chlorine dioxide may be useful in controlling periodontal biofilms but it is not definitive evidence that stabilized chlorine dioxide would produce an effective outcome on eliminating ONJ biofilms, which is currently hypothesized.

Hence, despite all of this evidence for how a stabilized chlorine dioxide source might facilitate resolution of ONJ, it is still not clear as to how or whether biofilms contribute to ONJ development and/or progression.

We claim:

1. A method for arresting and healing osteonecrosis of the jaw (ONJ) with a non-invasive procedure, said method comprising the steps of:
    (a) applying to ONJ tissues and lesions an alcohol free composition comprising a solution of a chlorine dioxide source having a concentration in the range of about 0.005% to about 2.0% weight/volume (w/v) selected from the group consisting of sodium chlorite, chlorite ion, and stabilized chlorine dioxide;
    (b) producing an antimicrobial effect against free-floating microorganisms that are present in lesions and tissues affected by ONJ;
    (c) penetrating, controlling or eliminating biofilm that forms over tissues affected by or susceptible to ONJ;
    (d) producing an antimicrobial effect against microorganisms present in biofilm formed over tissues affected by or susceptible to ONJ;
    (e) non-invasively debriding oral tissue affected by ONJ.

2. A method for penetrating, controlling and eliminating the biofilm associated with osteonecrosis of the jaw (ONJ), said method comprising the steps of:
    (a) applying to ONJ tissues and lesions an alcohol free a-composition comprising a solution of a chlorine dioxide source having a concentration in the range of about 0.005% to about 2.0% weight/volume (w/v) selected from the group consisting of sodium chlorite, chlorite ion, and stabilized chlorine dioxide;
    (b) producing an antimicrobial effect against free-floating microorganisms that are present in lesions and tissues affected by ONJ;
    (c) penetrating, controlling or eliminating biofilm that forms over tissues affected by or susceptible to ONJ;
    (d) producing an antimicrobial effect against microorganisms present in biofilm formed over tissues affected by or susceptible to ONJ;
    (e) non-invasively debriding oral tissue affected by ONJ.

3. A method for treating and arresting bisphosphonate-related osteonecrosis of the jaw (ONJ), said method comprising the steps of:
    (a) applying to ONJ tissues and lesions an alcohol free composition comprising a solution of a chlorine dioxide source having a concentration in the range of about 0.005% to about 2.0% weight/volume (w/v) selected from the group consisting of sodium chlorite, chlorite ion, and stabilized chlorine dioxide;
    (b) producing an antimicrobial effect against free-floating microorganisms that are present in lesions and tissues affected by ONJ;
    (c) penetrating, controlling or eliminating biofilm that forms over tissues affected by or susceptible to ONJ;
    (d) producing an antimicrobial effect against microorganisms present in biofilm formed over tissues affected by or susceptible to ONJ;
    (e) non-invasively debriding oral tissue affected by ONJ.

4. The method as set forth in claim 1 wherein said step of applying is carried out three times daily.

5. The method as set forth in claim 4 wherein each said step of applying is carried out for 30 seconds.

6. The method as set forth in claim 2 wherein said step of applying is carried out three times daily.

7. The method as set forth in claim 6 wherein each said step of applying is carried out for 30 seconds.

8. The method as set forth in claim 3 wherein said step of applying is carried out three times daily.

9. The method as set forth in claim 8 wherein each said step of applying is carried out for 30 seconds.

10. The method as set forth in claim 1 wherein the composition is in the form of a gel.

11. The method as set forth in claim 2 wherein the composition is in the form of a gel.

12. The method as set forth in claim 3 wherein the composition is in the form of a gel.

13. The method as set forth in claim 1 wherein the weight/volume (w/v) of the chlorine dioxide source is 0.10%.

14. The method as set forth in claim 2 wherein the weight/volume (w/v) of the chlorine dioxide source is 0.10%.

15. The method as set forth in claim 3 wherein the weight/volume (w/v) of the chlorine dioxide source is 0.10%.

16. The method as set forth in claim 1 including the step of closing the diseased area with no bone exposure.

17. The method as set forth in claim 2 including the step of closing the diseased area with no bone exposure.

18. The method as set forth in claim 3 including the step of closing the diseased area with no bone exposure.

\* \* \* \* \*